(12) United States Patent
Castillo-Welter et al.

(10) Patent No.: US 10,035,737 B2
(45) Date of Patent: Jul. 31, 2018

(54) PLANT AND PROCESS FOR PRODUCING PROPYLENE FROM METHANOL

(71) Applicant: L'Air Liquide, Societe Anonyme pour l'Etude et l'Exploitation des Procedes Georges Claude, Paris (FR)

(72) Inventors: Frank Castillo-Welter, Friedrichsdorf (DE); Stephane Haag, Frankfurt am Main (DE); Lin Lin, Frankfurt am Main (DE); Martin Rothamel, Frankfurt am Main (DE)

(73) Assignee: L'Air Liquide Societe Anonyme Pour L'Etude Et L'Exploitation Des Procedes Georges Claude, Paris (FR)

( * ) Notice: Subject to any disclaimer, the term of this patent is extended or adjusted under 35 U.S.C. 154(b) by 0 days.

(21) Appl. No.: 15/529,647

(22) PCT Filed: Dec. 15, 2015

(86) PCT No.: PCT/EP2015/025102
§ 371 (c)(1),
(2) Date: May 25, 2017

(87) PCT Pub. No.: WO2016/096154
PCT Pub. Date: Jun. 23, 2016

(65) Prior Publication Data
US 2017/0362141 A1    Dec. 21, 2017

(30) Foreign Application Priority Data
Dec. 18, 2014   (DE) .......................... 10 2014 118 967

(51) Int. Cl.
*C07C 1/20* (2006.01)
*B01J 8/02* (2006.01)
(Continued)

(52) U.S. Cl.
CPC ................. *C07C 1/20* (2013.01); *B01D 3/143* (2013.01); *B01D 3/40* (2013.01); *B01J 8/0278* (2013.01); *B01J 2208/00752* (2013.01)

(58) Field of Classification Search
CPC ........ C07C 1/20; C07C 11/02; C07C 2529/40; B01D 3/143; B01D 3/40; C10G 2300/807;
(Continued)

(56) References Cited

U.S. PATENT DOCUMENTS 9,724,620 B2 * 8/2017 Rothaemel ............. B01D 3/143

FOREIGN PATENT DOCUMENTS

| DE | 10 027 159 | 12/2001 |
| DE | 102 42 349 | 5/2003 |

(Continued)

OTHER PUBLICATIONS

International Search Report and Written Opinion for PCT/EP2015/025102, dated May 6, 2016.

*Primary Examiner* — Sharon Pregler
(74) *Attorney, Agent, or Firm* — Justin K. Murray (57) ABSTRACT

The present invention relates to a plant and a process for producing propylene at least one oxygenate, comprising a reactor for converting the reactant mixture into a product mixture which comprises propylene and also aliphatic and aromatic $C_{5+}$ hydrocarbons, at least one distillation column for removing a $C_{5+}$ stream, the $C_{5+}$ stream comprising at least 90 wt % of the aliphatic and aromatic $C_{5+}$ hydrocarbons of the product mixture, an extractive distillation column for separating the $C_{5+}$ stream into an aromatics stream and an aliphatics stream, the aliphatics stream comprising at least 90 wt % of the aliphatics of the $C_{5+}$ stream, and the aromatics stream comprising at least 90 wt % of the aromatics of the $C_{5+}$ stream, and an aliphatics recycle line for (Continued)

at least partial recycling of the aliphatics stream to the reactor. According to the invention, an aromatics recycle line is provided which returns the aromatics stream at least partially as extractant into the extractive distillation column.

17 Claims, 1 Drawing Sheet

(51) Int. Cl.
  *B01D 3/40* (2006.01)
  *B01D 3/14* (2006.01)
(58) Field of Classification Search
  CPC ........ C10G 2400/20; B01J 2208/00752; B01J 8/0278
  See application file for complete search history.

(56) References Cited

FOREIGN PATENT DOCUMENTS

| | | |
|---|---|---|
| DE | 10 2005 048931 | 4/2007 |
| DE | 10 2006 026103 | 12/2007 |
| DE | 10 2009 031636 | 1/2011 |

* cited by examiner

PLANT AND PROCESS FOR PRODUCING PROPYLENE FROM METHANOL

CROSS REFERENCE TO RELATED APPLICATIONS

This application is a § 371 of International PCT Application PCT/EP2015/025102, filed Dec. 15, 2015, which claims the benefit of DE 10 2014 118 967.1, filed Dec. 18, 2014, both of which are herein incorporated by reference in their entireties.

FIELD OF THE INVENTION

The present invention relates to a plant and a process for producing propylene from a reactant mixture comprising at least one oxygenate, comprising a reactor for converting the reactant mixture into a product mixture which comprises propylene and also aliphatic and aromatic $C_{5+}$ hydrocarbons, at least one distillation column for removing a $C_{5+}$ stream, the $C_{5+}$ stream comprising at least 90 wt % of the aliphatic and aromatic $C_{5+}$ hydrocarbons of the product mixture, an extractive distillation column for separating the $C_{5+}$ stream into an aromatics stream and an aliphatics stream, the aliphatics stream comprising at least 90 wt % of the aliphatics of the $C_{5+}$ stream, and the aromatics stream comprising at least 90 wt % of the aromatics of the $C_{5+}$ stream, and an aliphatics recycle line for at least partial recycling of the aliphatics stream to the reactor.

BACKGROUND

Propene ($C_3H_6$), often also referred to as propylene, is one of the most important starting materials in the chemical industry. It serves as a starting material for the production of chemicals such as acetone, acrylic acid, propylene oxide and acrolein, and therefore represents one of the most important basic chemicals in the chemical industry. Propylene is used, moreover, for the production of polypropylene (PP) plastics. The demand for the basic propylene chemical is increasing worldwide, with propylene, just like ethylene, being produced usually from petroleum in a steamcracker in a ratio which is dependent on the process and on the feedstocks.

In order to obtain additional propylene, there are a series of processes in existence, such as the PDH process, which starts from propane as reactant. Since, however, the greatest fraction of propylene continues to be produced by steam-cracking (around 70%), the tendency is to convert the $C_4$ to $C_8$ olefins produced in crackers or other petrochemical plants into additional propylene and also, in part, into ethylene.

This can be done, firstly, via the metathesis process, which is based on a synproportionation of ethylene and butylene. Disadvantages here are that it requires the build-up of ethylene production and that only certain $C_{4+}$ olefin isomers can be converted.

Also possible is an olefin conversion in which $C_{4+}$ olefins are reacted to give propylene. This cracking operation is accomplished by means of the Propylur or the OCP process, and is utilized in particular in order to utilize for propylene production the—comparatively low-value—$C_{4+}$ olefins that are produced in a cracker plant. Because of the endothermic nature of the reaction, however, the temperature in the reactor drops with ongoing conversion, and so limits the achievable propylene yield.

Appropriate, lastly, is the methanol-to-propylene process (also MTP® process), in which methanol/dimethyl ether or else other oxygenates are converted to propylene over a usually zeolitic catalyst.

The MTP process customarily has a propylene yield of about 65% (mole-C). For example, DE 10 027 159 A1 describes an MTP process with two shaft reactors. In a first, heterogeneously catalysed process step, methanol vapour is reacted to give dimethyl ether. This dimethyl ether is then divided into two substreams, which are supplied to respective first and second shaft reactors, in which a propylene-containing product mixture is produced over a zeolitic catalyst. Also introduced into the second shaft reactor, moreover, is the product stream of the first shaft reactor. As a result, a comparatively high propylene fraction of up to 50 vol % is achieved. At the same time, the process is very economic, given replacement of expensive tubular reactors by comparatively cost-effective shaft reactors.

DE 10 2006 026 103 A1 describes another type of reactor for implementing an MTP process. In this case, gaseous oxygenates are reacted together with steam at 400 to 470° C. in a closed reactor having a plurality of trays, to give olefins. The individual trays are filled with a fixed bed of catalyst. Each tray is fed individually with water and dimethyl ether and/or with a methanol-containing liquid phase, which is sprayed through a plurality of nozzle tubes. In this way, the optimum operating conditions for a stream with this degree of conversion can be set in each tray.

DE 10 2009 031 636, finally, describes a process for preparing the required oxygenates, more particularly methanol and dimethyl ether, which is designed in such a way as to allow flexible switching between methanol purification and production of dimethyl ether.

The MTP process is also described comprehensively in DE 10 2005 048 931 A1. Olefins are produced from a reactant mixture comprising steam and oxygenates, such as methanol and/or dimethyl ether. This reactant mixture is converted in at least one reactor, through a heterogeneously catalysed reaction, into a reaction mixture comprising low molecular mass olefins and gasoline hydrocarbons. By means of a suitable separation approach, higher-value olefins, particularly the $C_{5+}$ fraction, can be returned as a recycling stream at least partially into the reactor, and very largely converted into propylene, thereby raising the propylene yield. An attempt is made to remove the aromatics using a distillation column. This is necessary since otherwise the aromatics in the reactor react with short-chain olefins (ethylene, propylene and butylene) in a Friedel-Crafts alkylation and therefore diminish the propylene yield.

A disadvantage of this process is that the separation performance is not sufficient to achieve sufficient removal of the aromatics. A change to the distillation parameters, such as liquid-phase temperature or reflux rate, does not result in an improvement in the separation performance, since the boiling points of the components to be separated are too similar. A further hindrance is that the yield of aromatics fluctuates greatly in the MTP process. The aromatics fraction in the feed line to a corresponding separation means is typically between 1 to 50 wt %, in particular between 5 and 40 wt %. Accordingly, hydrocarbons, more particularly aliphatic hydrocarbons and especially olefins, having more than 7 carbon atoms ($C_{7+}$) have been withdrawn from the process together with the aromatics.

SUMMARY OF THE INVENTION

It is an object of the invention, therefore, to provide a plant and a process which achieve improved separation of aromatics and aliphatics and so permit recycling of long-chain, aliphatic hydrocarbons, and, correspondingly, achieve a boost in the propylene yield.

This object is achieved in accordance with the invention with a plant having the features of the claims.

In one embodiment of the present invention, a plant of for producing propylene from a reactant mixture comprising at least one oxygenate, comprises:
 a) a reactor for converting the reactant mixture into a product mixture which comprises propylene and also aliphatic and aromatic $C_{5+}$ hydrocarbons,
 b) at least one distillation column for removing a $C_{5+}$ stream, the $C_{5+}$ stream comprising at least 90 wt %, preferably ≥95 wt % and very preferably >98 wt % of the aliphatic and aromatic $C_{5+}$ hydrocarbons of the product mixture,
 c) an extractive distillation column for separating the $C_{5+}$ stream into an aromatics stream and an aliphatics stream, the aliphatics stream comprising at least 90 wt %, preferably ≥95 wt % and very preferably >98 wt % of the aliphatics of the $C_{5+}$ stream, the aromatics stream comprising at least 90 wt %, preferably ≥95 wt % and very preferably >98 wt % of the aromatics of the $C_{5+}$ stream,
 d) an aliphatics recycle line for at least partial recycling of the aliphatics stream to the reactor, and
 e) an aromatics recycle line, which returns the aromatics stream at least partially as extractant into the extractive distillation column.

The partial recycling of aromatics via the aromatics recycle line into the extractive distillation column produces improved separation between aliphatic and aromatic $C_{5+}$ hydrocarbons. This leads to a reduction in the aromatics fraction in the aliphatics stream and to an increase in the aromatics fraction in the bottom of the extractive distillation column. What makes this more surprising is that the recycled aromatics comprise a complex mixture of different aromatics (especially benzene, toluene and xylenes), and not a chemically pure extractant.

It has proved to be favourable to provide a separation device for removing residual aliphatics as a further aliphatics stream from the aromatics stream. This reduces the proportion of aliphatics in the aromatics stream. Because the aromatics stream is supplied as an extractant to the extraction column, a lower aliphatics fraction in the aromatics stream leads to a particularly good extraction activity of the aromatics in the extraction column.

The separation device may be an absorption column, a distillation column or an extraction column. The separation device in this case may in each case be configured in the form of a column.

The further aliphatics stream is preferably likewise fed into the reactor. In this case the yield of propylene can be further boosted.

There is preferably a second recycle line for at least partial recycling of the further aliphatics stream to the reactor. In principle, however, it is also conceivable for the further aliphatics stream to be passed into the reactor via the aliphatics return line.

It has further proved to be favourable if the aromatics are recycled above the feed entry within the extractive distillation column. As a result, the aliphatics taken off via the top of the extractive distillation column are not contaminated by the recycled aromatics. This ensures more particularly that there is a clean separation and there are constant separating conditions (especially pressure, temperature and composition of the stream to be separated).

Certain embodiments of the invention can further include a process for producing propylene having the features as disclosed herein.

In one embodiment, the process for producing propylene from a reactant mixture comprising at least one oxygenate, can include the following process steps:
 a) converting the reactant mixture in at least one reactor into a product mixture which comprises propylene and also aliphatic and aromatic $C_{5+}$ hydrocarbons,
 b) removing a $C_{5+}$ stream from the product mixture, the $C_{5+}$ stream comprising at least 90 wt %, preferably ≥95 wt % and very preferably >98 wt % of the aliphatic and aromatic $C_{5+}$ hydrocarbons of the product mixture,
 c) separating the $C_{5+}$ stream by means of extractive distillation into an aromatics stream and an aliphatics stream, the aliphatics stream comprising at least 90 wt %, preferably ≥95 wt % and very preferably >98 wt % of the aliphatics of the $C_{5+}$ stream, and the aromatics stream comprising at least 90 wt %, preferably ≥95 wt % and very preferably >98 wt % of the aromatics of the $C_{5+}$ stream,
 d) at least partially recycling the aliphatics stream to the reactor, where
 e) the aromatics stream is returned at least partially as extractant into process step c).

The separation of the $C_{5+}$ stream is preferably carried out at a temperature of 100 to 200° C. and/or under a pressure of 1 to 10 bar. These conditions have proved to be particularly suitable for the clean separation of the $C_{5+}$ stream into an aromatics stream and an aliphatics stream. In particular, the stated pressures and temperatures ensure that there is only a negligibly small fraction of aromatics in the aliphatics stream. Surprisingly, the recycling of the aromatics in accordance with the invention, via the aromatics recycle line, allows the regulation of pressure and temperature in the extractive distillation column, which previously—that is, without the recycling of the aromatics—did not achieve separation of aromatics and aliphatics.

The aromatics fraction in the aliphatics stream is preferably <5 wt %, more preferably <1 wt % and very preferably <0.1 wt %.

In one preferred refinement of the invention, a further aliphatics stream is removed from the aromatics stream. As a result of this, the aromatics stream supplied to process step c) contains a particularly small amount of aliphatics, specifically <10 wt %, preferably <5 wt % and more preferably <1 wt %. The lower fraction of aliphatics improves the extraction activity of the aromatics stream returned.

It is preferred for the further aliphatics stream to consist to an extent of at least 90 wt %, preferably ≥95 wt % and very preferably >98 wt % of aliphatic compounds having seven or more carbon atoms. With the present invention it is now possible even for such long-chain aliphatic compounds to be returned to the reactor and hence for the propylene yield to be further boosted.

In one preferred refinement of the invention, parts of the aromatics stream are withdrawn as a gasoline product stream from the process. This prevents accumulation of the aromatics in the plant. Furthermore, the aromatics obtained as a by-product can in this way be obtained as a product of value, thereby further enhancing the economics of the invention.

For the aliphatics recycling of the invention it has proven to be particularly favourable if in process step d) between 50 and 99.5 wt % of the aliphatics stream are recycled to the reactor. With this fraction, the conversion of long-chain aliphatics into short-chain olefins, more particularly propylene, is particularly efficient.

Preferably between 10 and 99.5 wt % of the aromatics stream are returned from the separation device (90) as extractant into the extracted distillation column. It has been found that with such a proportion of returned aromatics, the extraction ensues the most efficiently.

The temperature of introduction into the bottom of the extractive distillation column is preferably between 100 and 200° C., or between 120 and 170° C. As a result, the extractive distillation column can be operated with particular energy efficiency.

It has proved to be favourable, furthermore, if the temperature difference between top and bottom of the extractive distillation column is between 40 and 200° C., preferably 50 and 130° C. In this way, separation of aliphatic and aromatic $C_{5+}$ hydrocarbons can be very clean.

BRIEF DESCRIPTION OF THE DRAWINGS

Developments, advantages and application possibilities for the invention will become apparent as well from the description hereinafter of the drawing and of the working examples. All of the features described and/or pictorially depicted, on their own or in any desired combination, constitute the subject of the invention, irrespective of their summarizing in the claims or the dependency relationship therein.

DETAILED DESCRIPTION OF THE INVENTION

Figure 1:
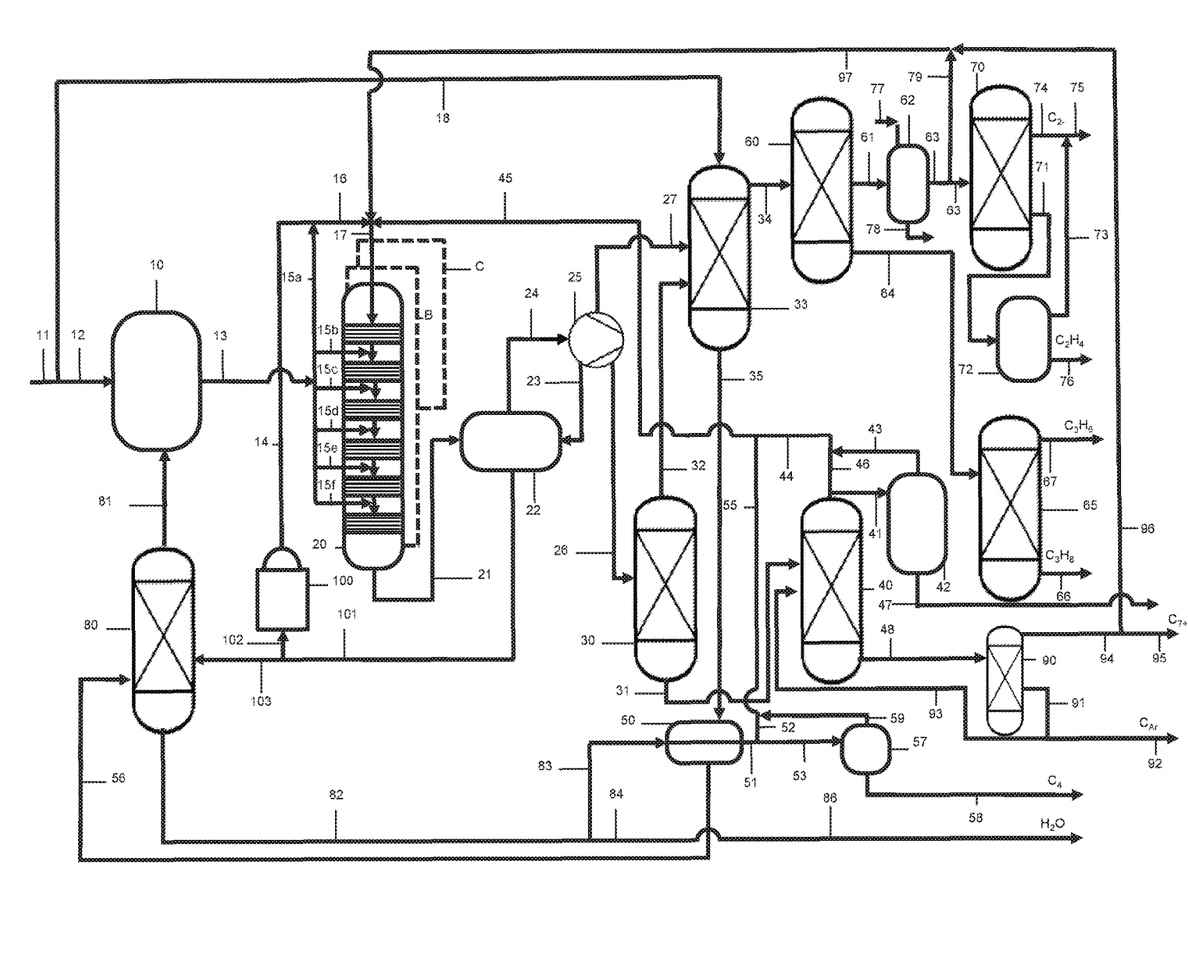
The FIGURE shows a plant of the invention for producing propylene, with inventive extractive distillation column and aromatics recycling.

The FIGURE shows the flow diagram for a plant, and of a process, for the production of propylene starting from methanol as reactant. The embodiment comprises six sections, these being a reaction zone, reactor regeneration (not shown), gas separation, hydrocarbon compression, a purification section (for propylene, liquefied petroleum gas (LPG) and gasoline hydrocarbons), and an ethylene recovery/cooling system.

The methanol reactant can be fed in either in purified form (preferably with the US Federal specification O-M-232L as grade AA) or as crude methanol, in either gaseous or liquid form. The reactant can also be used in each stated form as a solvent in the purification stages described later on below. Gaseous reactant is typically provided as gaseous methanol from an upstream methanol production facility. In liquid form, the methanol is typically provided from a purification column of the methanol production facility. Not only purified methanol but also crude methanol and the feeding thereof into a first reaction step can be carried out in the manner described for example in DE 10 2009 031 636. Alternatively, liquid methanol can also be produced directly in the plant of the invention.

The methanol is supplied via line 11 and 12 to a reactor 10 for producing dimethyl ether. Liquid methanol is initially fed in vaporized and superheated form, with a temperature of 250 to 280° C., into the dimethyl ether reactor 10.

The dimethyl ether reactor 10 may be configured as a one-stage adiabatic fixed bed reactor, in which case preferably an aluminium oxide catalyst is used for converting the methanol into dimethyl ether. In a similar way, however, it is also possible to use other catalysts, preferably zeolites such as dimensionally stable ZSM-5 zeolite.

The resultant dimethyl ether is supplied, together with unreacted methanol and also the water formed in the reaction, via the lines 13 and 14 to a distributor line, via which this intermediate can then be fed to each individual tray of a reactor 20 by means of the lines 15a, 15b, 15c, 15d, 15e and 15f. The feed to the first, topmost tray in this case is such that steam from the line 14 and recycled hydrocarbons from the line 45 are admixed additionally to the mixture passed through line 15a, and the resultant mixture is introduced in superheated form via line 17 into the reactor 20. The feeding of the steam from the line 14 also reduces the catalyst-damaging coking of the reactor.

The recycling of the hydrocarbons to the reactor 20 has the effect on the one hand of increasing the yield of propylene through conversion of the hydrocarbons, more particularly olefins, having a carbon number of less than or greater than three into propylene. The hydrocarbons also act as a heat sink and therefore improve temperature control over the reactor stages or the catalyst beds.

The pressure at which the reactant mixture is fed into the reactor is as low as possible, which increases the selectivity and hence the yield in respect of propylene. The designing of the reactor at pressures within the reactor which are below atmospheric pressure, however, becomes significantly more complicated. In addition, a pressure drop is observed across the individual reactor/catalyst stages and downstream plant components. Consequently, feed pressures of 0.1 to 2 barg, in other words 0.1 to 2 bar above the ambient pressure, have proved to be particularly favourable.

The reactor 20 here is designed preferably as a fixed bed reactor, as described in DE 10 027 159 or in DE 10 2006 026 103. The terms "shaft reactor" and "fixed bed reactor" are used synonymously in this context.

The reactor 20 used may be configured in duplicate or triplicate in the same way as is indicated by B and C. This offers the advantage that in one or more parallel-connected reactors, the dimethyl ether can be converted into olefins, while the catalyst is being regenerated in the other reactors. Accordingly, plant down times are avoided. It is also possible for more than three reactors to be used.

Reactor regeneration is carried out typically when the conversion of the oxygenates (especially dimethyl ether and methanol) falls below certain limit values. For the regeneration of the reactor, it is flushed with a nitrogen/air mixture, thereby achieving controlled combustion of the carbon deposits on the catalyst. The individual regeneration steps include the removal of the reactor from the MTP process (off-line connection), cleaning with steam, drying with nitrogen, and then the regeneration proper with a hot mixture of nitrogen and air.

The overall reaction of the conversion of the oxygenates to olefins in the reactor 20 is exothermic, and for this reason it is possible for cooling to be provided between the individual reactor trays, within the individual reactor trays and/or else in the reactor 20. Ideally, the cooling in each tray produces an optimum temperature profile, meaning that on entry into each tray a temperature of 400-480° C., preferably 420-470° C., is reached, and on exit, after the exothermic reactions have run their course, a temperature of 440-540° C., preferably 460-510° C., is attained.

One preferred possibility for cooling is the at least partial condensing of the stream 14 (i.e. of the stream conveyed in line 14), thus producing (not shown) a gaseous stream, which comprises DME, and a liquid stream, which comprises water and methanol. If a two-phase, i.e. gaseous and liquid, stream is fed to at least one of the reactor beds, the temperature within the individual reactor bed can be controlled through the ratio of the liquid phase to the gaseous phase, since a consequence of a liquid feed is evaporation within the stage, thereby removing heat from the system as a result of the enthalpy of vaporization, and thereby cooling the system. The temperature profile over the reactor stages or within the reactor 20 can be set precisely for each reactor stage via the temperature of the stream fed in and/or by the ratio of liquid phase to gaseous phase.

The introduction, as already addressed, of a steam-containing mixture into the reactor 20 via line 14, 16, 17 over the first reactor bed allows yet further control of the temperature profile, since the high heat capacity of the added steam allows it to act as a heat sink, and it reduces the reaction-related temperature increase. By virtue of an extremely homogeneous temperature profile within the individual reactor beds, unwanted secondary reactions, and especially the coking that harms the catalyst, are prevented, and the reactions are carried out within a temperature range which is optimal for maximizing the formation of olefin. The addition of water via lines 15b to 15f is generally unnecessary, since water is formed as a by-product within the reactor.

A product mixture (product stream) is then taken off from the reactor 20 via line 21, and comprises substantially olefins, steam, unconverted methanol and dimethyl ether, but also small amounts of naphthenes, paraffins and aromatics, propylene in particular, and also aliphatic and aromatic $C_{5+}$ hydrocarbons, other by-products such as butenes and butanes, and low boilers. Generally speaking, the olefins, apart from the propylene, are returned to the reactor 20 in order to increase the propylene yield.

The product mixture is generally cooled and then passed to a quench 22. Within the quench system, one or more water circuits cool the product mixture and cause substantial condensation of the water present, thereby removing said water from the hydrocarbons. As a result of the water formed in the reaction and the water recycled with stream 14, a methanol-containing water excess is produced in the quench circuit. This excess is taken off via line 97. The organic phase is passed via line 24 to a compressor 25.

Depending on the configuration of the quench system 22, a part of the hydrocarbons may also be obtained in the form of a liquid phase. These hydrocarbons are likewise passed to the further separating devices, more particularly the column 30, via a line which is not shown. For example, the quench system 22 may comprises a preliminary quench column and a main quench column.

The major part of the quench water is recirculated. The water heated in the quench system 22 can be used for heat recovery and employed in order to generate the steam which is fed into the reactor 20. The subsequent cooling takes place with a service steam, before the water is then returned into the quench system.

Formed as a further by-product of the reaction of the oxygenate stream are organic acids. It may therefore be useful to admix a pH-neutralizing chemical to the quench medium (water, for example), via a metering apparatus which is not shown, in order thus to neutralize the acids and to prevent corrosion of the plant components.

In order to avoid instances of poisoning of the catalyst by traces of sodium, for example, in the water it may be useful, moreover, to provide for distillation or an ion exchanger in order to purify the circulated water. This is especially useful before the generation of the steam which is fed subsequently into the reactor.

After the quenching system 22, line 24 supplies a gaseous organic fraction to the compressor 25, said fraction carrying at least 95 wt % of the olefins present in the product stream. Given that the gas is heated as a result of compression, moreover, it is useful to insert a heat exchanger—not shown—in the subsequent line 27 and accordingly to carry out cooling and at least partial condensation of the gas. One preferred embodiment uses four compressor stages, connected in series, and behind each compressor stage cools the gas and carries out its partial condensation. Through removal downstream of each individual compressor stage, a liquid fraction and a gaseous fraction can be obtained with comparatively precise separation.

The liquid fraction is separated into an aqueous phase and a hydrocarbon phase. This separation may be carried out after each individual compressor stage and/or after passage through all compressor stages and mixing at each of the streams obtained. The aqueous phase is returned via line 23 into the quench system 22.

In order to prevent accumulation of deposits within the at least one compressor 25, one preferred embodiment of the invention provides for a washing oil to be supplied to the at least one compressor 25. This may be done continuously or at intervals. The wash oil used preferably comprises light gasoline which is present in the process, in order not to introduce any additional compounds into the system.

If the removal of the oxygenates from the product stream proves to be unexpectedly problematic, it is possible, moreover, to insert an extraction and/or scrubbing—not shown—before or after the quench 22 and/or before or after the compressor 25. The resulting oxygenate-containing streams are supplied (not shown) to the methanol recovery system (e.g. the column 80).

The condensation itself allows a rough separation to be carried out, in dependence on the chain length of the hydrocarbons formed. This separation, though, is not selective for carbon compounds having four carbon atoms ($C_4$), which are therefore found in both fractions. The condensed, possibly reheated and consequently at least partly vaporized, $C_{4+}$ fraction is taken off via line 26. Line 27 supplies the $C_{4-}$ fraction, in other words carbon compounds having 4 carbon atoms or fewer, to a separating apparatus 33. In the separating apparatus 33, the $C_{3-}$ hydrocarbons are separated from the $C_{4+}$ hydrocarbons, the separation being carried out such that at least 95 wt % of the $C_3$ hydrocarbons (i.e. propylene and propane) present in stream 27 (i.e. the stream conveyed in the line 27) are located in stream 34 (i.e. the stream conveyed in line 34) and so at least 95 wt % of the $C_4$ hydrocarbons (butenes and butanes) present in stream 27 are located in stream 35 (i.e. the stream conveyed in line 35).

While the $C_{4+}$ fraction is supplied via line 35 to a mixer/settler 50, the $C_{3-}$ fraction is supplied via line 34 to a rectifying column 60. Before being fed into the rectifying column 60, the $C_{3-}$ fraction can be supplied to a drying apparatus. Furthermore, the $C_{3-}$ fraction can be cooled and so at least partly condensed before being supplied—in that case in at least partly liquid form—to the rectifying column 60.

It has proven to be particularly useful to configure the separating column 33 as an extractive distillation, and in one particularly preferred embodiment of the process, the extractant used is methanol, being already present in the process. The extractive distillation is carried out preferably as described in DE 10 2004 052 658 B3. The methanol used as reactant is preferably utilized and is fed into the column 33 via line 18. As a result, any dimethyl ether present is also removed.

When the preferably oxygenate-free $C_{3-}$ fraction has reached the separating column 60 via line 34, the $C_3$ fraction is separated therein from the $C_{2-}$ fraction. The pressure in the separating apparatus 60 must be adapted on the one hand such that a suitable cooling medium can be selected in the condenser assigned to the separating column 60, and on the other hand such that in the compressor upstream of the separating column 60, compression of the streams is possible. This problem scenario is associated with the extremely low boiling point at the $C_{2-}$ and $C_3$ streams, imposing great restrictions on the selection of cooling media which are preferably liquid at the temperatures in question. One possibility of resolving this problem scenario lies in operating the separation apparatus 30, 33 and 60 at approximately 20 bar and in using, in the condenser of the separation apparatus 60, a cooling medium whose boiling point is well below the boiling point of propylene (−48° C. at 1 bar(a), 49° C. at 20 bar(a)). A second possibility is to operate the separation apparatus 33 and 60 under a pressure which allows the same coolant, namely propylene, to be used in both separation apparatus 33 and 60 and in the associated condensers, which are not shown. A third possibility is to operate all of the serially connected separation apparatus 30, 33 and 60 at approximately 20 bar and to use a compressor only in the top stream from the separation apparatus 60, in order for propylene to be employed as cooling medium in the condenser of the separation apparatus 60.

The $C_{2-}$ fraction taken off preferably at the top of the separation column 60 is passed via line 61 into a $CO_2$ separator 62. In order to remove the $CO_2$, as a minor but unwanted by-product, use may be made of one or more alkali metal or alkaline earth metal hydroxide solutions, which are supplied via line 77 and are contacted with the gas stream in the separator 62. They react with the carbon dioxide passed through the separator, forming carbonates which remain in the aqueous phase and which are extracted with the spent hydroxide solution via line 78. Generally speaking, an additional, final demineralized water wash solution, preferably as the last operation, is used in order to prevent penetration of the $CO_2$.

The $C_{2-}$ fraction purified in this way is supplied subsequently via line 63 to a separating column 70, configured more particularly as a rectifying column, in which a fraction comprising substantially methane is taken off at the top as low boilers. The separating conditions within the column 70 are selected such that at least 95 wt % of the ethylene present in stream 63 (i.e. the stream conveyed in line 63) is present in stream 71 (i.e. the stream conveyed in line 71).

Following $CO_2$ removal, a partial stream, optionally enriched with ethylene, is supplied via lines 79, 97 back to the reactor 20. In this way it is possible on the one hand to increase the propylene yield. On the other hand, the production quantity of ethylene can be regulated in this way.

Via line 71, the bottom product is fed into a $C_2$ splitter 72, in which, first, the valuable ethylene product is taken off via line 76 and, secondly, ethane is admixed via line 73 to the line 74 and so taken off via line 75. This gas may be utilized, for example, as an energy source elsewhere in the operation, or else sold. The ethylene obtained is immediately suitable for the production of polyethylene.

The $C_{2-}$ stream from lines 73, 74 and/or 75 can be returned wholly or partly, via a line which is not shown, back into the reactor 20. This on the one hand allows the propylene yield to be increased, and on the other hand allows the production quantity of ethylene to be regulated.

A further possibility is to take off a $C_{2-}$ stream at various points in the process. For example, the $C_{2-}$ stream can be taken off as non-condensing gas from the rectifying column 60. If $CO_2$ has to be removed from the $C_{2-}$ stream taken off accordingly, low boilers can be accumulated by partial condensation, with $CO_2$ remaining in gaseous form and being amenable to extraction.

Since the quantity of ethene product in the MTP process is usually low, one process variant shuns the purification of the ethene and generates exclusively a recycle stream which is depleted in $CO_2$ and enriched in ethene, and which is supplied to the reactor 20. Water and $CO_2$ absolutely must be removed before the stream is supplied to the separation column 70, since otherwise ice, dry ice and/or $CO_2$ hydrates are formed, and block the plant.

The $C_3$ fraction is passed from column 60, via line 64, into the column 65, which is configured preferably as a rectifying column. From this column 65, propane is taken off via the bottom and via line 66. The valuable propylene product is taken off via the top of the column 65 and via line 67. Depending on requirements imposed on the propylene, particularly in the case of subsequent reaction to form polypropylene, there may be further downstream purification steps.

Additionally, a $C_{4+}$ fraction is taken off from the bottom of column 30, via line 31, and then passes into the extractive distillation column 40. From this column, an aromatics stream is taken off at the bottom via line 48. Additionally, an aliphatics stream is taken off at the top. The column 30 here is operated such that at least 50 wt %, preferably more than 90 wt %, of the $C_5$ hydrocarbons present in stream 31 (i.e. the stream conveyed in line 31) pass into the stream 46 (i.e. the stream conveyed in line 46); additionally, at least 50 wt %, preferably more than 75 wt %, of $C_6$ hydrocarbons present in stream 31 pass into the stream 46. Moreover, less than 10 wt %, preferably less than 5 wt %, of the $C_6$ and $C_7$ aromatics (substantially benzene, toluene and xylene) present in the stream 31 are to pass into the stream 46.

At the top of the extractive distillation column 40 it is also possible for an aliphatic $C_{7+}$ fraction to be removed. In that case the stream 46 additionally comprises at least 25 wt %, preferably more than 50 wt %, of the aliphatic $C_7$ hydrocarbons present in the stream 31.

At least a portion of the aliphatics stream in line 46 is then supplied via line 41 to a gasoline stabilizer 42. Here, a portion of the comparatively light, aliphatic $C_5$-$C_7$ components is removed from line 41 in a targeted way, and taken off via line 47. It is also possible to admix parts of the aromatics in lines 48 or 92 to the stream in line 47 (not shown). Accordingly, as and when necessary, the vapour pressure of the resultant mixture, which leaves the plant confines as a gasoline product via line 47, can be adjusted to a higher value which is necessary to suit particular specifications, in accordance with EN 228, for example. Furthermore, any $C_4$ hydrocarbons still present can be admixed via line 43, from the gasoline stabilizer 42, to the stream from line 47 (not shown).

The fraction comprising aliphatic $C_{5+}$ hydrocarbons passes via line 43 into line 44 and from there into line 45, where it is fed into the reactor 20.

The aromatics stream taken off from the extractive distillation column 40 is supplied preferably via line 48 to a separation device 90. In the separation device 90, aliphatic $C_{7+}$ hydrocarbons are removed from the aromatics stream and are taken off via lines 94 and 95. A partial stream of these aliphatic $C_{7+}$ hydrocarbons may also be supplied via line 96 to the line 97 and so introduced again into the reactor 20.

It is useful to remove a part of the aliphatic $C_{7+}$ hydrocarbons from the process via line 95, since otherwise there would be a build-up of inert constituents within the process.

The aromatics stream, purified to remove aliphatic $C_{7+}$ hydrocarbons, is taken off from the separation device 90 via line 91. A partial stream thereof is removed from the process via line 92 and can be supplied (not shown), for example, to the gasoline hydrocarbons taken off from line 47. The remaining part is supplied as extractant via line 93 to the extractive distillation column 40.

As a result of the recycling of the aromatics to the extractive distillation column 40, the separation performance of the extractive distillation column 40 is significantly improved. A build-up of the aromatics in the column bottom is achieved.

In the mixer/settler 50, the $C_4$ fraction from the column 30 is mixed thoroughly with water (from line 83), and, after a resting phase, two phases are formed. An aqueous phase, containing oxygenates such as methanol and DME, is removed and supplied via line 56 to methanol recovery.

The organic phase, containing the $C_4$ fraction, is withdrawn via line 51.

Optionally, and depending on plant requirements, a part of the $C_4$ fraction may be returned to the reactor 20 as recycle via the line 52, 45 and 17. This may be useful especially when coproduction of propylene and butenes is to be carried out in the plant. A maximum of 90 wt % of the $C_4$ fraction is returned, and in the minimum case there is no recycling at all (0 wt %).

A low level of recycling of the $C_4$ fraction may lead to an unfavourable change in the temperature profile within the reactor 20. This disadvantage can be compensated, however, by the recycle of the $C_{5+}$, the $C_{5/6}$ and/or the $C_{7+}$ fraction and also by the deliberate recycle of butanes.

Accordingly, stream 53 (i.e. the stream conveyed in line 53), which includes not only olefinic but also paraffinic $C_4$ hydrocarbons, may be supplied optionally to a suitable separation device 57, where methods known to the skilled person are used to carry out rough separation between butanes and the other $C_4$ components. In the present case, separation by membrane is particularly appropriate, since stream 53 arrives at an elevated pressure of at least 10 bar, and so the pressure difference between retentate side and permeate side that is advantageous for the performance of the membrane is already present and would not have to be first brought about by means of additional pumps or compressors.

The butane-rich, water-free fraction of low methanol content leaves the separation device 57 via the stream 59 (i.e. the stream conveyed in line 59) and is returned back into the reactor together with stream 52 (i.e. the stream conveyed in line 52) via line 55.

It is also possible (not shown) to combine the butane-rich fraction in line 59 together with the propane from line 66 and to take them off jointly from the process as autogas (liquefied petroleum gas, LPG).

The low-butane fraction leaves the separation device 57 via the stream 58 (i.e. the stream conveyed in line 58). A further purification of the $C_4$ fraction, which comprises 1-butene, isobutene, cis-2-butene, trans-2-butene and also traces of butadiene, is not shown, but is usually carried out. Separation into the individual isomers and the removal of the butadiene are known from the literature (e.g. Frank Gehlen et al.: "Butenes" in Ullmann's Encyclopedia of Industrial Chemistry, published online 31 Jan. 2014). Butadiene is removed customarily by extraction, using NMP (N-methylpyrrolidone), for example, as extractant. Isobutene is notable for its relatively high chemical reactivity, and can, for example, be converted into methyl tert-butyl ether (MTBE) by etherification with methanol over a suitable catalyst, by reactive distillation, and removed.

The methanol-containing and DME-containing aqueous stream that is taken off from the mixer-settler 50 via line 56 is fed via line 56 into the methanol recovery column 80. One of the streams taken off from this methanol recovery column, via line 81, is a methanol-rich top stream, which is passed into the reactor 10 for reaction of methanol to give dimethyl ether. As a result, unreacted oxygenates can be recovered from the aqueous methanol solution and supplied to the reactor 20. A water stream, heavily depleted of organic impurities such as DME or methanol, is taken off from the bottom via line 82 and is used again in part via line 83 for the mixer/settler. The remaining water residue is extracted via line 86 and can be used both within and outside the plant.

In a manner not shown, excess water can also be used as cooling water in at least one component, such as a reactor 10, 20, or else in the condensers—not shown—of the subsequently described separating columns 30, 33, 40, 60, 65 and/or 70. Further applications of excess water include the following: cooling water feed, recycle to upstream synthesis gas production and/or rinse water.

Furthermore, the methanol recovery column 80 is fed by the aqueous methanol fraction from the quench 22 via line 101, 103. The methanol recovery column 80 could additionally be supplied with oxygenate-containing streams for other extraction apparatus, not shown, such apparatus being used typically for the removal of oxygenates from the product streams (for example, from lines 58, 66, 67, 75, 76, 95 and 92). The feed of the various streams into the methanol recovery column 80 is generally optimized in such a way that the separation performance of the column 80 is optimized.

From the aqueous methanol solution, via line 102, parts of this stream are supplied to a steam generator 100, from which steam is taken off via line 14 and is supplied via lines 16 and 17 to the reactor 20.

Depending on the optimization of the methanol recovery system and according to the desired product properties, the methanol recovery column 80 may also have an additional, assigned stripping column (not shown) for extraction of the water. Provided in general, therefore, is a methanol recovery column 80, or a methanol recovery column 80 with stripping column for water extraction.

Very generally, in the condensers, heaters of the corresponding separation devices 30, 40, 42 and/or in the separation devices themselves, polymerization inhibitors may be added but prevent thermally induced polymerization of the olefins. This provision may of course also be made accordingly, where necessary, in the separation apparatus 33, 60, 70, 72, 65 and/or 90.

Since the recycling of hydrocarbons to the reactor 20 plays an important part in the production of propylene in the MTP process, both the flow rate and the composition of the overall stream returned ought to be monitored and regulated. In general the MTP process may be designed in such a way that the ratio of the amount of recycled hydrocarbons to the amount of methanol supplied to the reactor is 0 to 3 t/t. A preferred ratio is from 0.75 to 1.5 t/t. The subdivision of these streams over the different reactor stages may also be adapted in order to maximize the propylene yield and the catalyst service life.

The advantages of the invention are to be described using the working examples below.

WORKING EXAMPLES

The basis for the examples below is a feed flow to the column of 1000 kg/h.
Feed Composition

| Olefins/ (kg/h) | Aromatics/ (kg/h) | Paraffins kg/h | Cyclo-paraffins/ (kg/h) | Cyclo-olefins/ (kg/h) |
|---|---|---|---|---|
| 325.5 | 105.3 | 458.4 | 101.8 | 9.0 |

Table 1 shows a typical composition of the top stream (aliphatics stream) of a distillation column without inventive recycling of the aromatics stream as extractant.

TABLE 1

Top stream of the distillation column - not inventive

| $T_{bottom}$/ °C. | Olefins/ (kg/h) | Aromatics/ (kg/h) | Paraffins kg/h | Cyclo-paraffins/ (kg/h) | Cyclo-olefins/ (kg/h) |
|---|---|---|---|---|---|
| 126 | 299.9 | 1.6 | 431 | 87.7 | 9.0 |
| 128 | 304.1 | 1.6 | 432.9 | 88.1 | 9.0 |
| 132 | 310.5 | 2.5 | 435.4 | 89.7 | 9.0 |
| 136 | 311.5 | 8.6 | 440.4 | 92.4 | 9.0 |
| 140 | 331.6 | 13.7 | 444.3 | 93.4 | 9.0 |
| 142 | 311.7 | 14.0 | 449.9 | 93.7 | 9.0 |
| 144 | 315.9 | 14.1 | 453.1 | 94.5 | 9.0 |
| 150 | 325.4 | 23.9 | 458.5 | 99.0 | 9.0 |

Table 2 shows a typical composition of the top stream of a distillation column (see above) without inventive recycling of the aromatics stream as extractant.

TABLE 2

Bottom stream of the distillation column - not inventive

| $T_{bottom}$/ °C. | Olefins/ (kg/h) | Aromatics/ (kg/h) | Paraffins kg/h | Cyclo-paraffins/ (kg/h) | Cyclo-olefins/ (kg/h) |
|---|---|---|---|---|---|
| 126 | 25.6 | 103.7 | 27.4 | 14.1 | <0.1 |
| 128 | 21.3 | 103.6 | 25.7 | 13.7 | <0.1 |
| 132 | 15.0 | 102.8 | 22.9 | 12.2 | <0.1 |
| 136 | 13.9 | 94.7 | 19.9 | 9.5 | <0.1 |
| 140 | 14.0 | 91.5 | 14.2 | 8.4 | <0.1 |
| 142 | 13.8 | 91.2 | 8.6 | 8.1 | <0.1 |
| 144 | 9.6 | 91.1 | 5.4 | 7.3 | <0.1 |
| 150 | 0.016 | 81.4 | <0.1 | 2.8 | <0.1 |

Table 3 shows a typical composition of the top stream (aliphatics stream) of an extractive distillation column with inventive recycling of the aromatics stream as extractant.

TABLE 3

Top stream of the extractive distillation column - inventive

| Recycle quantity/ (kg/h) | $T_{bottom}$/ °C. | Olefins/ (kg/h) | Aromatics/ (kg/h) | Paraffins kg/h | Cyclo-paraffins/ (kg/h) | Cyclo-olefins/ (kg/h) |
|---|---|---|---|---|---|---|
| 60 | 132 | 297.7 | 1.5 | 430.2 | 87.4 | 9.0 |
| 70 | 136 | 304.0 | 1.6 | 432.5 | 88.1 | 9.0 |
| 110 | 140 | 305.2 | 1.7 | 433.1 | 88.3 | 9.0 |
| 130 | 142 | 306.3 | 1.7 | 433.8 | 88.4 | 9.0 |
| 150 | 144 | 307.6 | 1.8 | 434.3 | 88.6 | 9.0 |
| 150 | 150 | 311.5 | 9.3 | 439.2 | 92.5 | 9.0 |

Table 4 shows a typical composition of the bottom stream of an extractive distillation column with inventive recycling of the aromatics stream as extractant.

TABLE 4

Bottom stream of the extractive distillation column - inventive

| Recycle quantity/ (kg/h) | $T_{bottom}$/ °C. | Olefins/ (kg/h) | Aromatics*/ (kg/h) | Paraffins kg/h | Cyclo-paraffins/ (kg/h) | Cyclo-olefins/ (kg/h) |
|---|---|---|---|---|---|---|
| 60 | 132 | 27.8 | 163.8 (103.8) | 28.2 | 14.4 | <0.1 |
| 70 | 136 | 21.5 | 173.6 (103.6) | 25.8 | 13.9 | <0.1 |
| 110 | 140 | 20.2 | 213.6 (103.6) | 25.3 | 13.6 | <0.1 |
| 130 | 142 | 19.1 | 233.5 (103.5) | 24.8 | 13.4 | <0.1 |
| 150 | 144 | 17.8 | 253.4 (103.4) | 24.3 | 13.2 | <0.1 |
| 150 | 150 | 13.9 | 245.9 (95.9) | 19.4 | 9.3 | <0.1 |

*Quantity of aromatics in the bottom stream corresponds to the total aromatics stream minus the returned aromatics stream employed as extractant.

In comparison to the process without recycling of the aromatics-rich stream as extractant, a reduction in the fraction of aromatics in the low-aromatics stream is apparent, to 1.5 kg/h (from 2.5 kg/h) at 132° C. up to a reduction to 1.8 kg/h (from 14.1 kg/h) at 144° C.

In the aromatics-rich stream, in contrast, an intended increase is achieved in the fraction of aromatics, to 163.8 kg/h (from 102.8 kg/h) at 132° C. up to an increase of 253.4 kg/h (from 91.1 kg/h) at 144° C.

It is clear, furthermore, that an increase in the temperature of the bottoms above 144° C. does not permit a further improvement in the process.

Table 5 shows a comparison of the fractions of the aromatics in the top stream (aliphatic stream) with and without recycling of the aromatics stream as extractant.

TABLE 5

Comparison of the top streams for exemplary temperatures

| $T_{bottom}$/ °C. | Amount of recycled aromatics stream/ (kg/h) | Aromatics$_{without\ recycling}$/ (kg/h) | Aromatics$_{with\ recycling}$/ (kg/h) | Change/ % |
|---|---|---|---|---|
| 132 | 60 | 2.5 | 1.5 | 40 |
| 144 | 150 | 14.1 | 1.8 | 87 |

These FIGURES demonstrate yet again that for the two temperatures selected exemplarily, a reduction is achieved in the aromatics in the top stream (aliphatics stream) of the extractive distillation column.

Table 6 shows a comparison of the fractions in the bottom stream of the extractive distillation column with and without recycling of the aromatics as extractant.

TABLE 6

Comparison of the bottom streams for exemplary temperatures with and without aromatics recycling

| Example | $T_{bottom}$/ °C. | Aromatics in bottoms*/ (kg/h) | Olefin (kg/h) | Olefin gain/ % |
|---|---|---|---|---|
| 1- comparative (without aromatics recycling) | 128 | 103.6 | 21.3 | — |
| 2- Invention | 144 | 103.4 | 17.8 | 16.4 |
| 3- Invention | 150 | 95.9 | 13.9 | 34.7 |

*corrected for recycle stream

The comparison of Example 1 (not inventive) with Examples 2 and 3 (inventive) shows the better olefin removal in accordance with the invention achieved through aromatics recycling.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

LIST OF REFERENCE SYMBOLS

10 Reactor
11-19 Line
20 Reactor
21 Line
22 Quench
23, 24 Line
25 Compressor
26, 27 Line
30 Distillation column
31, 32 Line
33 Distillation column
34, 35 Line
40 Distillation column
40a Extractive distillation column
41 and 41a Line
42 and 42a Gasoline stabilizer
43-49 Line
43a-46a Line
50 Mixer/settler
51-56 Line
57 Distillation column
58-59 Line
60 Separating column
61 Line
62 $CO_2$ separator
63, 64 Line
65 Column
66-69 Line
70 Distillation column
71-79 Line
80 Separation apparatus
81-86 Line
90 Separation device
91-97 Line
100 Steam generation
101-103 Line

The invention claimed is:

1. A plant for producing propylene from a reactant mixture comprising at least one oxygenate, the plant comprising:

a) a reactor configured to convert the reactant mixture into a product mixture which comprises propylene and also aliphatic and aromatic $C_{5+}$ hydrocarbons,
b) a distillation column configured to remove a $C_{5+}$ stream, the $C_{5+}$ stream comprising at least 90 wt % of the aliphatic and aromatic $C_{5+}$ hydrocarbons of the product mixture;
c) an extractive distillation column configured to separate the $C_{5+}$ stream into an aromatics stream and an aliphatics stream, the aliphatics stream comprising at least 90 wt % of the aliphatics of the $C_{5+}$ stream, and the aromatics stream comprising at least 90 wt % of the aromatics of the $C_{5+}$ stream;
d) an aliphatics recycle line configured to at least partial recycle the aliphatics stream to the reactor; and
e) an aromatics recycle line configured to return the aromatics stream at least partially as extractant into the extractive distillation column.

2. The plant according to claim 1, further comprising a separating device configured to remove remaining aliphatics as a further aliphatics stream from the aromatics stream.

3. The plant according to claim 2, wherein the separating device is an absorption column, a distillation column or an extraction column.

4. The plant according to claim 2, further comprising a second recycle line configured to at least partial recycle the further aliphatics stream to the reactor.

5. The plant according to claim 2, wherein the aromatics recycle line opens into the bottom of the extractive distillation column.

6. A process for producing propylene from a reactant mixture comprising at least one oxygenate, the process comprising the following steps:
a) converting the reactant mixture in at least one reactor into a product mixture which comprises propylene and also aliphatic and aromatic $C_{5+}$ hydrocarbons;
b) removing a $C_{5+}$ stream from the product mixture, the $C_{5+}$ stream comprising at least 90 wt % of the aliphatic and aromatic $C_{5+}$ hydrocarbons of the product mixture;
c) separating the $C_{5+}$ stream by means of extractive distillation into an aromatics stream and an aliphatics stream, the aliphatics stream comprising at least 90 wt % of the aliphatics of the $C_{5+}$ stream, and the aromatics stream comprising at least 90 wt % of the aromatics of the $C_{5+}$ stream;
d) at least partially recycling the aliphatics stream to the reactor; and
e) returning the aromatics stream at least partially as extractant into process step c).

7. The process according to claim 6, wherein the separation of the $C_{5+}$ stream is carried out at a temperature of 120 to 160° C. and/or under a pressure of 1 to 10 bar.

8. The process according to claim 6, wherein the separation of the $C_{5+}$ stream is carried out under a pressure of 1 to 6 bar.

9. The process according to claim 6, wherein a further aliphatics stream is removed from the aromatics stream.

10. The process according to claim 9, wherein the further aliphatics stream consists to an extent of at least 90 wt % of aliphatic compounds having seven or more carbon atoms.

11. The process according to claim 6, wherein parts of the aromatics stream are withdrawn as a gasoline product stream.

12. The process according to claim 6, wherein in process step d) between 50% and 99.5% of the aliphatics stream are recycled to the reactor.

13. The process according to claim 6, wherein between 50 and 99.5 wt % of the aromatics stream are returned from the separation device as extractant into the extractive distillation column.

14. The process according to claim 6, wherein the temperature of introduction into the bottom of the extractive distillation column is between 100 and 200° C.

15. The process according to claim 6, wherein the temperature of introduction into the bottom of the extractive distillation column is between 120 and 170° C.

16. The process according to claim 6, wherein the temperature difference between top and bottom of the extractive distillation column is between 40 and 200° C.

17. The process according to claim 6, wherein the temperature difference between top and bottom of the extractive distillation column is between 50 and 130° C.

* * * * *